(12) United States Patent
Mathis et al.

(10) Patent No.: US 6,824,562 B2
(45) Date of Patent: Nov. 30, 2004

(54) BODY LUMEN DEVICE ANCHOR, DEVICE AND ASSEMBLY

(75) Inventors: Mark L. Mathis, Kirkland, WA (US); Leonard Kowalsky, Bothell, WA (US); David G. Reuter, Bothell, WA (US); Cruz Beeson, Kirkland, WA (US)

(73) Assignee: Cardiac Dimensions, Inc., Kirkland, WA (US)

( * ) Notice: Subject to any disclaimer, the term of this patent is extended or adjusted under 35 U.S.C. 154(b) by 79 days.

(21) Appl. No.: 10/142,637

(22) Filed: May 8, 2002

(65) Prior Publication Data

US 2003/0212453 A1 Nov. 13, 2003

(51) Int. Cl.[7] .................................................. A61F 2/06
(52) U.S. Cl. ...................... 623/2.36; 623/1.36; 623/1.11
(58) Field of Search ............................... 623/1.1, 1.11, 623/2.1, 2.11, 2.36, 2.37, 902, 12, 11.11, 66.1, 1.36, 1.23; 128/898; 606/108, 151–156, 191–198; 600/16, 36, 37

(56) References Cited

U.S. PATENT DOCUMENTS

| | | |
|---|---|---|
| 4,055,861 A | 11/1977 | Carpentier et al. |
| 4,164,046 A | 8/1979 | Cooley |
| 4,485,816 A | 12/1984 | Krumme |
| 4,550,870 A | 11/1985 | Krumme et al. |
| 4,830,023 A | 5/1989 | de Toledo et al. |
| 5,061,277 A | 10/1991 | Carpentier et al. |
| 5,250,071 A | 10/1993 | Palermo |
| 5,261,916 A | 11/1993 | Engelson |
| 5,265,601 A | 11/1993 | Mehra |
| 5,350,420 A | 9/1994 | Cosgrove et al. |
| 5,514,161 A | 5/1996 | Limousin |
| 5,554,177 A | 9/1996 | Kieval et al. |
| 5,562,698 A | 10/1996 | Parker |
| 5,584,867 A | 12/1996 | Limousin et al. |
| 5,601,600 A | 2/1997 | Ton |

(List continued on next page.)

FOREIGN PATENT DOCUMENTS

| | | |
|---|---|---|
| WO | WO-2000/044313 A1 | 8/2000 |
| WO | WO 00/60995 | 10/2000 |
| WO | WO-2001/000111 A1 | 1/2001 |
| WO | WO-2001/050985 A1 | 7/2001 |
| WO | WO 01/54618 A1 | 8/2001 |
| WO | WO-2001/087180 A2 | 11/2001 |
| WO | WO-2002/000099 A2 | 1/2002 |
| WO | WO-2002/001999 A2 | 1/2002 |
| WO | WO-2002/005888 A1 | 1/2002 |
| WO | WO-2002/019951 A1 | 3/2002 |
| WO | WO-2002/034118 A2 | 5/2002 |
| WO | WO-2002/047539 A2 | 6/2002 |
| WO | WO-2002/062263 A2 | 8/2002 |
| WO | WO-2002/062270 A1 | 8/2002 |
| WO | WO-2002/062408 A2 | 8/2002 |
| WO | WO-2002/076284 A2 | 10/2002 |
| WO | WO-2002/078576 A2 | 10/2002 |
| WO | WO-2002/096275 A2 | 12/2002 |
| WO | WO-2003/015611 A2 | 2/2003 |
| WO | WO-2003/049647 A1 | 6/2003 |
| WO | WO-2003/059198 A2 | 7/2003 |

*Primary Examiner*—David J. Isabella
*Assistant Examiner*—Urmi Chattopadhyay
(74) *Attorney, Agent, or Firm*—Wilson Sonsini Goodrich & Rosati

(57) ABSTRACT

An anchor anchors a therapeutic device having an elongated body within a body lumen. The anchor includes a fixation member carried on the device which is adjustable from a first configuration that permits placement of the device in the body lumen to a second configuration that anchors the device within the body lumen. The anchor further includes a lock that locks the fixation member in the second configuration. The fixation member may be locked in any one of a plurality of intermediate points between the first configuration and a maximum second configuration.

14 Claims, 4 Drawing Sheets

U.S. PATENT DOCUMENTS

| | | | |
|---|---|---|---|
| 5,733,325 | A | 3/1998 | Robinson et al. |
| 5,824,071 | A | 10/1998 | Nelson et al. |
| 5,895,391 | A | 4/1999 | Farnholtz |
| 5,908,404 | A | 6/1999 | Elliot |
| 5,961,545 | A * | 10/1999 | Lentz et al. ............... 623/1.39 |
| 5,984,944 | A | 11/1999 | Forber |
| 6,027,517 | A | 2/2000 | Crocker et al. |
| 6,077,295 | A | 6/2000 | Limon et al. |
| 6,077,297 | A | 6/2000 | Robinson et al. |
| 6,099,549 | A | 8/2000 | Bosma et al. |
| 6,099,552 | A * | 8/2000 | Adams ...................... 606/220 |
| 6,129,755 | A | 10/2000 | Mathis et al. |
| 6,190,406 | B1 | 2/2001 | Duerig et al. |
| 6,210,432 | B1 | 4/2001 | Solem et al. |
| 6,275,730 | B1 | 8/2001 | KenKnight et al. |
| 6,342,067 | B1 | 1/2002 | Mathis et al. |
| 6,352,553 | B1 | 3/2002 | van der Burg et al. |
| 6,352,561 | B1 | 3/2002 | Leopold et al. |
| 6,395,017 | B1 | 5/2002 | Dwyer et al. |
| 6,402,781 | B1 * | 6/2002 | Langberg et al. .......... 623/2.36 |
| 6,419,696 | B1 | 7/2002 | Ortiz et al. |
| 6,442,427 | B1 | 8/2002 | Boute et al. |
| 6,503,271 | B2 | 1/2003 | Duerig et al. |
| 6,537,314 | B2 | 3/2003 | Langberg et al. |
| 6,569,198 | B1 | 5/2003 | Wilson et al. |
| 6,589,208 | B2 * | 7/2003 | Ewers et al. ............... 604/104 |
| 6,602,288 | B1 | 8/2003 | Cosgrove et al. |
| 6,602,289 | B1 | 8/2003 | Colvin et al. |
| 6,623,521 | B2 * | 9/2003 | Steinke et al. ............. 623/1.16 |
| 6,626,899 | B2 | 9/2003 | Houser et al. |
| 6,716,158 | B2 | 4/2004 | Raman et al. |
| 6,718,985 | B2 | 4/2004 | Hlavka et al. |
| 6,723,038 | B1 | 4/2004 | Schroeder et al. |
| 2001/0018611 | A1 | 8/2001 | Solem et al. |
| 2001/0049558 | A1 | 12/2001 | Liddicoat et al. |
| 2002/0035361 | A1 | 3/2002 | Houser et al. |
| 2002/0042621 | A1 | 4/2002 | Liddicoat et al. |
| 2002/0042651 | A1 | 4/2002 | Liddicoat et al. |
| 2002/0049468 | A1 | 4/2002 | Streeter et al. |
| 2002/0055774 | A1 | 5/2002 | Liddicoat |
| 2002/0065554 | A1 | 5/2002 | Streeter |
| 2002/0087173 | A1 | 7/2002 | Alferness et al. |
| 2002/0095167 | A1 | 7/2002 | Liddicoat et al. |
| 2002/0103533 | A1 | 8/2002 | Langberg et al. |
| 2002/0138044 | A1 | 9/2002 | Streeter et al. |
| 2002/0151961 | A1 | 10/2002 | Lashinski et al. |
| 2002/0169502 | A1 | 11/2002 | Mathis |
| 2002/0169504 | A1 | 11/2002 | Alferness et al. |
| 2002/0183835 | A1 | 12/2002 | Taylor et al. |
| 2002/0183836 | A1 | 12/2002 | Liddicoat et al. |
| 2002/0183837 | A1 | 12/2002 | Streeter et al. |
| 2002/0183838 | A1 | 12/2002 | Liddicoat et al. |
| 2002/0183841 | A1 | 12/2002 | Cohn et al. |
| 2003/0018358 | A1 | 1/2003 | Saadat |
| 2003/0078465 | A1 | 4/2003 | Pai et al. |
| 2003/0078654 | A1 | 4/2003 | Taylor et al. |
| 2003/0083538 | A1 * | 5/2003 | Adams et al ................. 600/16 |
| 2003/0105520 | A1 * | 6/2003 | Alferness et al. .......... 623/2.36 |
| 2003/0130730 | A1 | 7/2003 | Cohn et al. |
| 2003/0130731 | A1 | 7/2003 | Vidlund et al. |
| 2003/0135267 | A1 | 7/2003 | Solem et al. |
| 2003/0144697 | A1 | 7/2003 | Mathis et al. |
| 2003/0171776 | A1 | 9/2003 | Adams et al. |
| 2003/0171806 | A1 | 9/2003 | Mathis et al. |
| 2004/0019377 | A1 | 1/2004 | Taylor et al. |
| 2004/0039443 | A1 | 2/2004 | Solem et al. |
| 2004/0073302 | A1 | 4/2004 | Rourke et al. |

* cited by examiner

BODY LUMEN DEVICE ANCHOR, DEVICE AND ASSEMBLY

FIELD OF THE INVENTION

The present invention generally relates to an anchor for use with a device which requires anchoring in a body lumen. The present invention more particularly relates to a mitral valve annulus device and assembly wherein the device is deployed and anchored in the coronary sinus of a heart adjacent the mitral valve annulus to reshape the mitral valve annulus.

BACKGROUND OF THE INVENTION

The human heart generally includes four valves. Of these valves, a most critical one is known as the mitral valve. The mitral valve is located in the left atrial ventricular opening between the left atrium and left ventricle. The mitral valve is intended to prevent regurgitation of blood from the left ventricle into the left atrium when the left ventricle contracts. In preventing blood regurgitation the mitral valve must be able to withstand considerable back pressure as the left ventricle contracts.

The valve cusps of the mitral valve are anchored to muscular wall of the heart by delicate but strong fibrous cords in order to support the cusps during left ventricular contraction. In a healthy mitral valve, the geometry of the mitral valve ensures that the cusps overlie each other to preclude regurgitation of the blood during left ventricular contraction.

The normal functioning of the mitral valve in preventing regurgitation can be impaired by dilated cardiomyopathy caused by disease or certain natural defects. For example, certain diseases may cause dilation of the mitral valve annulus. This can result in deformation of the mitral valve geometry to cause ineffective closure of the mitral valve during left ventricular contraction. Such ineffective closure results in leakage through the mitral valve and regurgitation. Diseases such as bacterial inflammations of the heart or heart failure can cause the aforementioned distortion or dilation of the mitral valve annulus. Needless to say, mitral valve regurgitation must not go uncorrected.

One method of repairing a mitral valve having impaired function is to completely replace the valve. This method has been found to be particularly suitable for replacing a mitral valve when one of the cusps has been severely damaged or deformed. While the replacement of the entire valve eliminates the immediate problem associated with a dilated mitral valve annulus, presently available prosthetic heart valves do not possess the same durability as natural heart valves.

Various other surgical procedures have been developed to correct the deformation of the mitral valve annulus and thus retain the intact natural heart valve function. These surgical techniques involve repairing the shape of the dilated or deformed valve annulus. Such techniques, generally known as annuloplasty, require surgically restricting the valve annulus to minimize dilation. Here, a prosthesis is typically sutured about the base of the valve leaflets to reshape the valve annulus and restrict the movement of the valve annulus during the opening and closing of the mitral valve.

Many different types of prostheses have been developed for use in such surgery. In general, prostheses are annular or partially annular shaped members which fit about the base of the valve annulus. The annular or partially annular shaped members may be formed from a rigid material, such as a metal, or from a flexible material.

While the prior art methods mentioned above have been able to achieve some success in treating mitral regurgitation, they have not been without problems and potential adverse consequences. For example, these procedures require open heart surgery. Such procedures are expensive, are extremely invasive requiring considerable recovery time, and pose the concomitant mortality risks associated with such procedures. Moreover, such open heart procedures are particularly stressful on patients with a compromised cardiac condition. Given these factors, such procedures are often reserved as a last resort and hence are employed late in the mitral regurgitation progression. Further, the effectiveness of such procedures is difficult to assess during the procedure and may not be known until a much later time. Hence, the ability to make adjustments to or changes in the prostheses to obtain optimum effectiveness is extremely limited. Later corrections, if made at all, require still another open heart surgery.

An improved therapy to treat mitral regurgitation without resorting to open heart surgery has recently been proposed. This is rendered possible by the realization that the coronary sinus of a heart is near to and at least partially encircles the mitral valve annulus and then extends into a venous system including the great cardiac vein. As used herein, the term "coronary sinus" is meant to refer to not only the coronary sinus itself but in addition, the venous system associated with the coronary sinus including the great cardiac vein. The therapy contemplates the use of a device introduced into the coronary sinus to reshape and advantageously effect the geometry of the mitral valve annulus.

The device includes a resilient member having a cross sectional dimension for being received within the coronary sinus of the heart and a longitudinal dimension having an unstressed arched configuration when placed in the coronary sinus. The device partially encircles and exerts an inward pressure on the mitral valve. The inward pressure constricts the mitral valve annulus, or at least a portion of it, to essentially restore the mitral valve geometry. This promotes effective valve sealing action and eliminates mitral regurgitation.

The device may be implanted in the coronary sinus using only percutaneous techniques similar to the techniques used to implant cardiac leads such as pacemaker leads. One proposed system for implanting the device includes an elongated introducer configured for being releasably coupled to the device. The introducer is preferably flexible to permit it to advance the device into the heart and into the coronary sinus through the coronary sinus ostium. To promote guidance, an elongated sheath is first advanced into the coronary sinus. Then, the device and introducer are moved through a lumen of the sheath until the device is in position within the coronary sinus. Because the device is formed of resilient material, it conforms to the curvatures of the lumen as it is advanced through the sheath. The sheath is then partially retracted to permit the device to assume its unstressed arched configuration. Once the device is properly positioned, the introducer is then decoupled from the device and retracted through the sheath. The procedure is then completed by the retraction of the sheath. As a result, the device is left within the coronary sinus to exert the inward pressure on the mitral valve to restore mitral valve geometry.

The foregoing therapy has many advantages over the traditional open heart surgery approach. Since the device, system and method may be employed in a comparatively noninvasive procedure, mitral valve regurgitation may be treated at an early stage in the mitral regurgitation progression. Further, the device may be placed with relative ease by any minimally invasive cardiologist. Still further, since the heart remains completely intact throughout the procedure, the effectiveness of the procedure may be readily determined. Moreover, should adjustments be deemed desirable, such adjustments may be made during the procedure and before the patient is sent to recovery.

Another approach to treat mitral regurgitation with a device in the coronary sinus is based upon the observation that the application of a localized force against a discrete portion of the mitral valve annulus can terminate mitral regurgitation. This suggests that mitral regurgitation may be localized and nonuniform. Hence, the device applies a force to one or more discrete portions of the atrial wall of the coronary sinus to provide localized mitral valve annulus reshaping instead of generalized reshaping of the mitral valve annulus. Such localized therapy would have all the benefits of the generalized therapy. In addition, a localized therapy device may be easier to implant and adjust.

A still further approach to treat mitral regurgitation from the coronary sinus of the heart contemplates a device having a first anchor configured to be positioned within and fixed to the coronary sinus of the heart adjacent the mitral valve annulus within the heart, a cable fixed to the first anchor and extending proximally from the first anchor within the heart, a second anchor configured to be positioned in and fixed in the heart proximal to the first anchor and arranged to slidingly receive the cable, and a lock that locks the cable on the second anchor. When the first and second anchors are fixed within the heart, the cable may be drawn proximally and locked on the second anchor. The geometry of the mitral valve is thereby effected. This approach provides flexibility in that the second anchor may be positioned and fixed in the coronary sinus or alternatively, the second anchor may be positioned and fixed in the right atrium. This approach further allows adjustments in the cable tension after implant.

A still further alternative for treating mitral regurgitation contemplates a device having a first anchor configured to be positioned within and anchored to the coronary sinus of the heart adjacent the mitral valve annulus within the heart. A second anchor is configured to be positioned within the heart proximal to the first anchor and adjacent the mitral valve annulus within the heart. A connecting member, having a fixed length, is permanently attached to the first and second anchors. As a result, when the first and second anchors are within the heart with the first anchor anchored in the coronary sinus, the second anchor may be displaced proximally to effect the geometry of the mitral valve annulus and released to maintain the effect on the mitral valve geometry. The second anchor may be configured, when deployed, to anchor against distal movement but be moveable proximally to permit the second anchor to be displaced proximally within the coronary sinus.

A further device that effects the condition of a mitral valve annulus of a heart also includes an elongated member dimensioned to be placed in the coronary sinus of the heart adjacent the mitral valve annulus. Here, the elongated member is flexible when placed in the heart in a first orientation to position the device in the coronary sinus adjacent the mitral valve annulus and relatively inflexible when rotated into a second orientation after the device is positioned in the coronary sinus adjacent to the mitral valve annulus.

The device thus has a first radius of curvature when in the first orientation and a second and greater radius of curvature when in the second orientation to effect the mitral valve geometry. Once positioned and in the second orientation, the device is anchored against both longitudinal and rotational movement.

Devices, other than those described above may be placed in body lumens other than the coronary sinus for therapeutic effect. All such devices must be anchored against movement when deployed at least for an acute phase until the natural body mechanisms produce sufficient fibrotic tissue about the devices for permanent fixation. While the device anchors must protect against device movement, they must also allow ready deployment to facilitate device implant. However, it is desirable that the anchors also be readily releasable, at least during the acute phase to permit device position adjustment or even device removal if required. All of these factors are especially important for devices implanted in the heart because of the potential need for precise device positioning during implant and the extreme movement of the heart during heartbeats.

SUMMARY OF THE INVENTION

The invention provides an anchor that anchors a device having an elongated body in a body lumen. The anchor includes a fixation member carried on the device, the fixation member being adjustable from a first configuration that permits placement of the device in the body lumen to a second configuration that anchors the device within the body lumen, and a lock that locks the fixation member in the second configuration.

The lock is releasable to release the fixation member from the second configuration to permit the device to be removed from the body lumen. The fixation member may also be deformable to permit the device to be moved within the body lumen.

The fixation member is adjustable from the first configuration to a maximum second configuration. The lock may be configured to lock the fixation member at any one of a plurality of intermediate points between the first configuration and the maximum second configuration.

The fixation member may be elongated and have a first end hingedly coupled to the device body. The fixation member may thus extend along the device body closely spaced to the device body when in the first configuration and be pivoted from the device body to the second configuration to engage and anchor the device in the body lumen.

The anchor may further include a support that renders the fixation member substantially rigid when in the second configuration. The support may be an extension of the fixation member, wherein the fixation member includes a second end opposite the first end and wherein the lock locks the fixation member second end on the device body.

The fixation member may include a second end opposite the first end. The support may include a support member having a first end hingedly coupled to the fixation member second end and a second end opposite the support member first end. The lock may lock the support member second end on the device body. The support member second end may be slidable along the device body. The anchor may include a plurality of the fixation members and/or a plurality of support members.

The invention further provides a device that effects the condition of a mitral valve annulus of a heart. The device includes an elongated body dimensioned to be placed in the coronary sinus of the heart adjacent the mitral valve annulus. The device further includes a fixation member carried by the device, the fixation member being adjustable from a first configuration that permits placement of the device in the coronary sinus to a second configuration that anchors the device within the coronary sinus, and a lock that locks the fixation member in the second configuration.

The lock is releasable to release the fixation member from the second configuration to permit the device to be moved within the coronary sinus. The fixation member may be deformable to permit the device to be moved within the coronary sinus.

The fixation member may be adjustable from the first configuration to a maximum second configuration and the lock may lock the fixation member at any one of a plurality of intermediate points between the first configuration and the maximum second configuration.

The fixation member is elongated and has a first end hingedly coupled to the device body. The fixation member may extend along the device body closely spaced to the device body when in the first configuration and may be pivoted from the device body when in the second configuration to engage the coronary sinus and anchor the device in the coronary sinus. The device may further include a support that renders the fixation member substantially rigid when in the second configuration. The support may be an extension of the fixation member, wherein the fixation member includes a second end opposite the first end and wherein the lock locks the fixation member second end on the device body. The fixation member second end may be slidable along the device body and the device may include a plurality of the fixation members.

The fixation member may include a second end opposite the first end. The support may be a separate support member having a first end hingedly coupled to the fixation member second end and second end opposite the support member first end. The lock may then lock the support member second end on the device body. The support member second end may be slidable along the device body. The device may include a plurality of the fixation members and support members.

The invention further provides an assembly that effects the condition of a mitral valve annulus of a heart. The assembly includes a mitral valve therapy device dimensioned to be placed in the coronary sinus adjacent the mitral valve annulus. The device includes an elongated body, a fixation member carried by the device, the fixation member being adjustable from a first configuration that permits placement of the device in the coronary sinus to a second configuration that anchors the device within the coronary sinus, and a lock that locks the fixation member in the second configuration. The assembly further includes a flexible catheter having a lumen that receives the device and being dimensioned to be advanced into the coronary sinus to place the device adjacent the coronary sinus.

The assembly may further include an elongated pusher that is received by the lumen of the catheter proximal to the device and that permits the device and the catheter to be moved opposite each other. The assembly may further include a tether receivable by the catheter lumen and engagable with the device to pull the device distally with respect to the catheter. The catheter may be used to transition the fixation member from the first configuration to the second configuration. For example, the fixation member may be elongated and have a first end hingedly coupled to the device body. The fixation member may then extend along the device body when in the first configuration and the fixation member may be pivoted from the device body into the second configuration by distal movement of the catheter with respect to the device to cause the fixation member to engage the coronary sinus and anchor the device in the coronary sinus.

BRIEF DESCRIPTION OF THE DRAWINGS

The features of the present invention which are believed to be novel are set forth with particularity in the appended claims. The invention, together with further aspects and advantages thereof, may best be understood by making reference to the following description taken in conjunction with the accompanying drawings, in the several figures of which like reference numerals identify identical elements, and wherein:

DETAILED DESCRIPTION OF THE INVENTION

Figure 1:
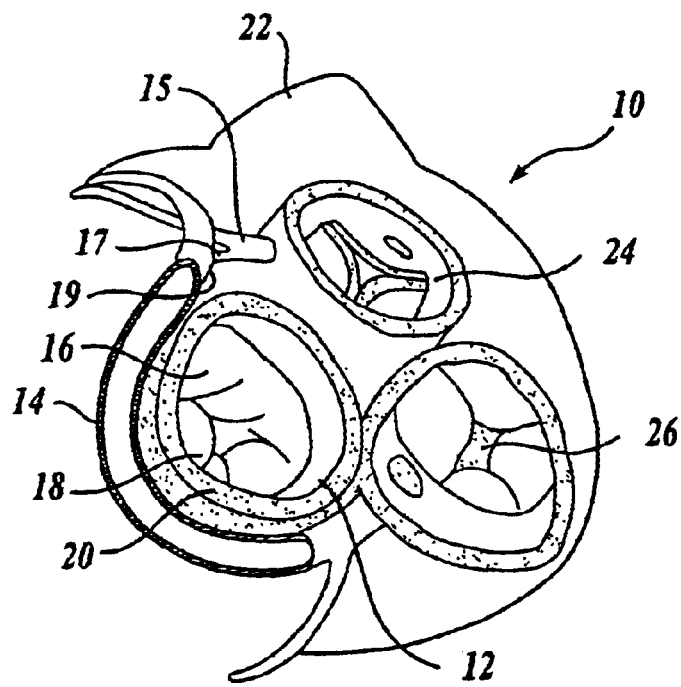
FIG. 1 is a superior view of a human heart with the atria removed.

Referring now to FIG. 1, it is a superior view of a human heart 10 with the atria removed to expose the mitral valve 12, the coronary sinus 14, the coronary artery 15, and the circumflex artery 17 of the heart 10 to lend a better understanding of the present invention. Also generally shown in FIG. 1 are the pulmonary valve 22, the aortic valve 24, and the tricuspid valve 26 of the heart 10.

The mitral valve 12 includes an anterior cusp 16, a posterior cusp 18 and an annulus 20. The annulus encircles the cusps 16 and 18 and maintains their spacing to provide a complete closure during a left ventricular contraction. As is well known, the coronary sinus 14 partially encircles the mitral valve 12 adjacent to the mitral valve annulus 20. As is also known, the coronary sinus is part of the venus system of the heart and extends along the AV groove between the left atrium and the left ventricle. This places the coronary sinus essentially within the same plane as the mitral valve annulus making the coronary sinus available for placement of the mitral valve therapy device of the present invention therein.

Figure 2:
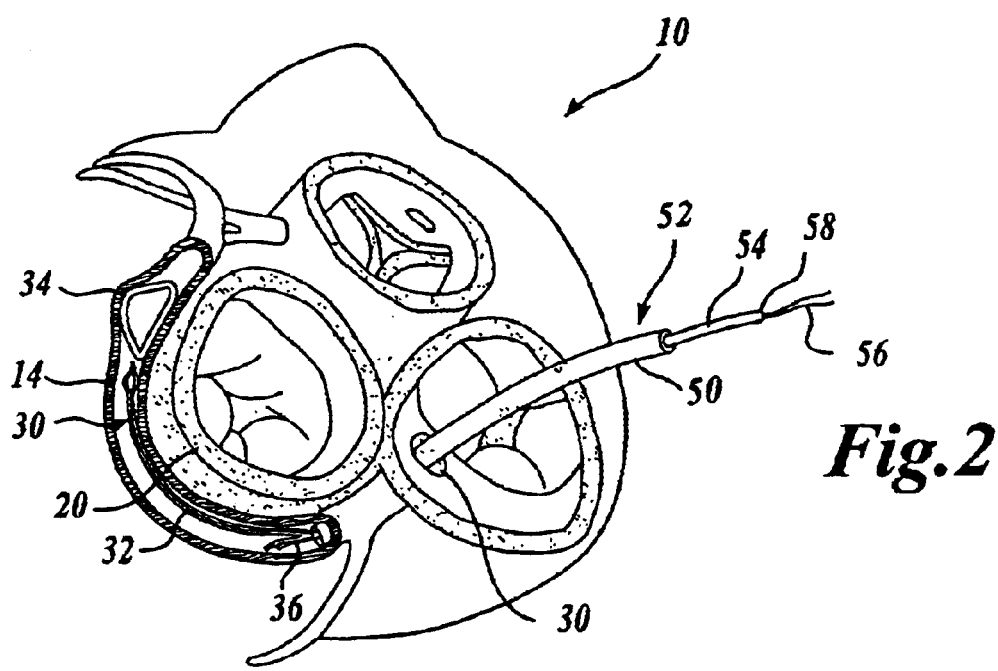
FIG. 2 is a superior view of a human heart similar to FIG. 1 illustrating a mitral valve therapy device including an anchor embodying the present invention deployed therein along with an assembly embodying the present invention for deploying the device.

FIG. 2 shows a mitral valve therapy device 30 embodying the present invention shown deployed in the coronary sinus 14 of the heart 10 adjacent the mitral valve annulus 20 for effecting the geometry of the mitral valve annulus. Also shown in FIG. 2 is a deployment system 50 that deploys the device 30 in the coronary sinus 14. The device 30 takes the form of an elongated body 32 which includes a distal anchor 34 embodying the present invention and a proximal anchor 36.

The anchors 34 and 36 are shown in FIG. 2 in their deployed configuration. As will be seen hereinafter, upon deployment of the device 30 in the coronary sinus, the distal anchor 34 is transitioned from a first configuration to a locked second configuration. In the process, it is expanded outwardly to anchor the device in the coronary sinus against both bi-directional longitudinal and rotational movement. The proximal anchor however, when deployed, is configured to permit proximal movement. This allows the device 30 to be tightened within the coronary sinus by proximal pulling of the anchor 36 after the distal anchor 34 is deployed. The device 30 may be formed from Nitinol or stainless steel, for example.

The deployment system 52 illustrated in FIG. 2 includes an elongated catheter 50, an elongated pusher 54, and a tether 56. In deploying the device 30, the tether 56 is first looped about the proximal anchor 36 of the device 30 as illustrated and the device is then loaded into the catheter 50. The tether 56 is then threaded through an internal lumen 58 of the pusher 54 and looped around the proximal anchor 36 of the device 30 as illustrated. The pusher 54 is then advanced along the tether 56 for engaging the device 30 and pushing the device distally down the catheter to a predetermined position at the distal end of the catheter 50. The catheter with the device 30 loaded therein is then fed into the heart and through the coronary sinus ostium 31 into the coronary sinus to place the catheter in a position such that the device 30 is adjacent the mitral valve annulus 20. Thereafter, the device is maintained in a stationary position by the pusher 54 as the catheter 50 is partially withdrawn to expose the distal anchor 34. Once the distal anchor is exposed, it is deployed by the catheter in a manner to be described more particularly with respect to FIGS. 3–6. Once the distal anchor 34 is deployed, the catheter 50 is then retracted proximally of the proximal anchor 36. This exposes the proximal anchor 36 and permits the proximal anchor to self deploy. Once the proximal anchor is deployed, the tether 56 is pulled proximally to move the proximal anchor 36 in a proximal direction for tightening the device within the coronary sinus and to an extent which results in the desired effect on the geometry of the mitral valve annulus 20. During this adjustment process, mitral regurgitation may be monitored and the device adjusted for optimal results. When the device 30 is in its final position within the coronary sinus 14, the pusher 54 and catheter 50 may be removed from the heart. The tether 56 may be permitted to remain in the heart during an acute phase to ascertain the effectiveness of the device 30. Should further adjustment of the device be necessary, the tether 56 may then be used as a guide for guiding the introduction of the catheter 50 back into the heart.

FIGS. 3–6 illustrate the manner in which the distal anchor 34 may be deployed in the coronary sinus 14 for anchoring the device 30. It will be appreciated by those skilled in the art, of course, that the anchor 34 may be utilized in body lumens other than the coronary sinus and with therapeutic devices other than the mitral valve annulus therapy device illustrated in FIG. 2.

Figure 3:
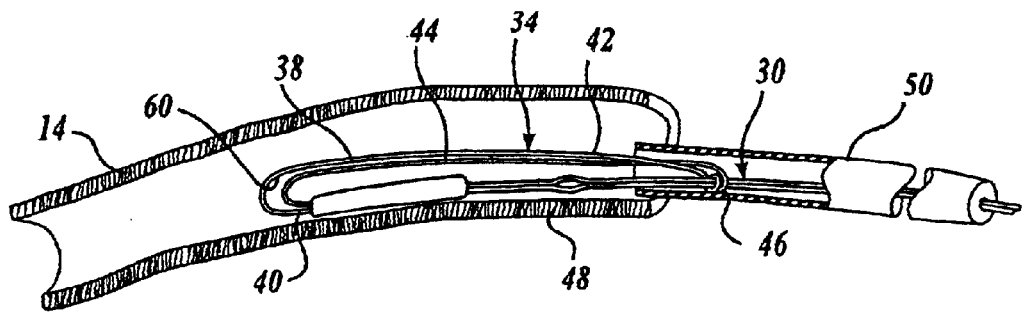
FIG. 3 is a side view with portions cut away illustrating a first step in deploying the device anchor of the device of FIG. 2.

In each of FIGS. 3–6 a portion of the coronary sinus has been removed and the pusher has not been illustrated so as to not unduly complicate the figures. FIG. 3 shows the catheter 50 disposed within the coronary sinus 14 with the device 30 and distal anchor within the catheter 50. To that end, the catheter includes a lumen 60 which is dimensioned to receive the device 30 and the distal anchor 34 when the distal anchor 34 is in a first configuration. The distal anchor 34 includes an elongated fixation member 38 which is hingedly coupled to the distal end of the device 30 at a hinge 40. The elongated fixation member thus extends along the body of the device 30. The fixation member includes a support 42 which is an extension of the fixation member 38 and which is hingedly connected to the fixation member 38 at a hinge point 44. The proximal end of the fixation member 38 includes a loop 46 which is looped about the device 30 to permit the loop 46 to slide along the device 30. As will be seen subsequently, the loop 46 forms part of a lock for locking the anchor 34 in a second configuration for anchoring in the coronary sinus.

To complete the anchor, the device 30 includes a resilient enlarged portion 48 over which the loop 46 may slide. Once the loop 46 is located distally of the enlarged portion 48, it will be held by the enlarged portion 48 for locking the device in the second configuration.

Figure 4:
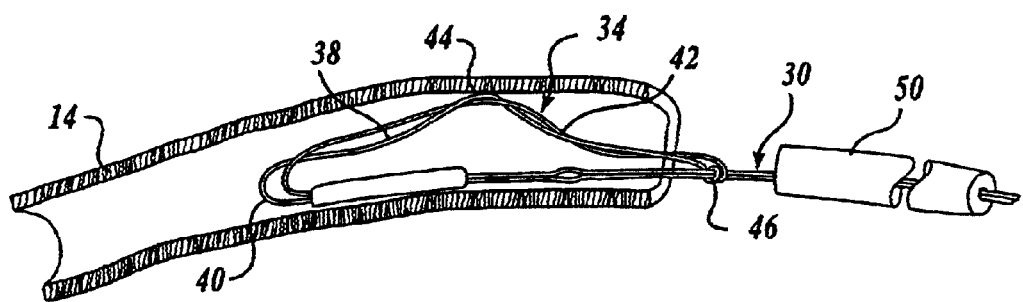
FIG. 4 is a side view similar to FIG. 3 illustrating a further step in the deployment of the anchor embodying the present invention.

FIG. 4 illustrates the anchor 34 after the catheter 50 has been moved proximal to the anchor 34. More specifically, it will be noted that the distal end of the catheter 50 is now proximal to the loop 46 or proximal end of the anchor 34. The shape memory of the anchor has caused the anchor to expand and is now partially transitioned from the first configuration of FIG. 3 to the second and final configuration to be described with reference to FIG. 6 subsequently.

Figure 5:
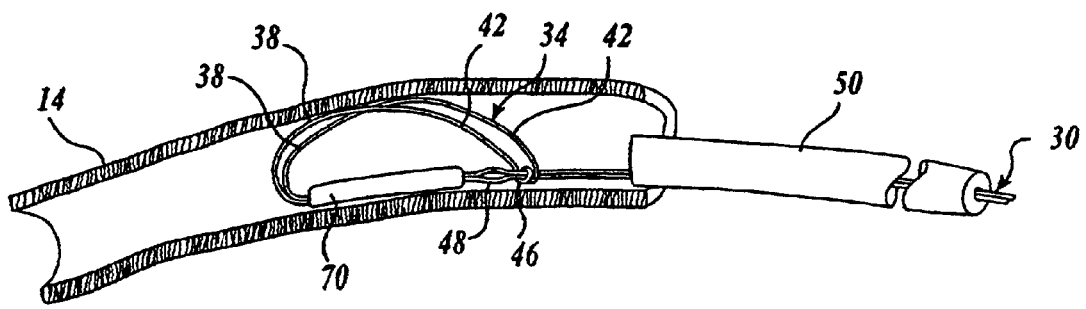
FIG. 5 is a side view similar to FIG. 3 illustrating a further step in the deployment of the device anchor.

FIG. 5 illustrates the anchor 34 being transitioned from the first configuration to the second configuration. This transition is implemented by the distal end of the catheter 50 pushing the proximal end of the anchor 34 in the distal direction. To maintain the position of the anchor 34 during the transition, the tether 56 is used to hold the device 30 against distal movement.

The particular configuration of the distal anchor 34 in accordance with this embodiment may be more particularly seen in FIG. 5. Here it may be seen that the distal anchor is formed of a wire having a first end secured to the distal end of the device 30, folded back and looped around the device and then back to the distal end of the device. Both ends of the anchor are then crimped by a crimp 70. This configuration results in a pair of fixation members 38 each having a support extension 42. In addition, the fixation members 38 may be formed so as to have a loop configuration to maximize surface contact with the inner wall of the coronary sinus 14.

Figure 6:
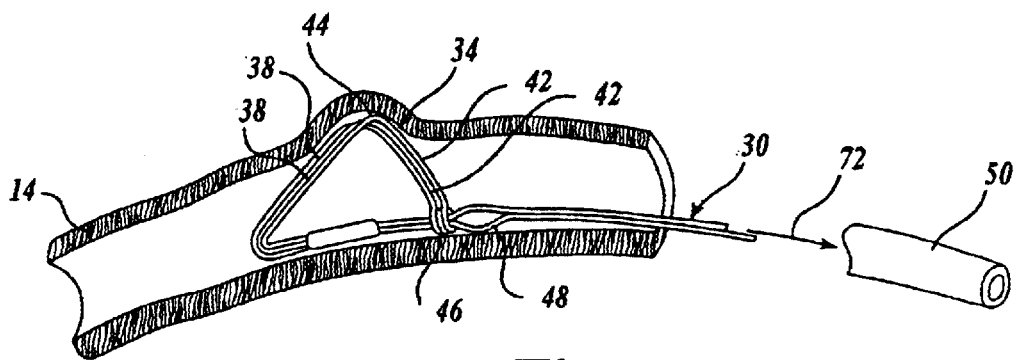
FIG. 6 is a side view similar to FIG. 3 illustrating the deployed device anchor.

As the catheter 50 is moved distally, it forces the loop 46 of the anchor 34 over the enlarged portion 48 of the device 30 to a point distal to the enlarged portion 48. This locks the loop 46 distally of the enlarged portion 48 for locking the anchor 34 in an enlarged second configuration as illustrated in FIG. 6 to anchor the device 30 within the coronary sinus 14. More specifically, it may be seen that the supports 42 have been pivoted at the hinge 44 relative to the fixation member 38. This allows the fixation members 38 to be supported by the supports 42 and securely locked by the lock of the loop 46 and enlarged portion 48 of the device 30. The fixation members 38 provide broad surface contact with the inner wall of the coronary sinus 14. This provides for anchoring within the coronary sinus of the device 30 against both bi-directional longitudinal and rotational movement. Once the anchor 34 is deployed as illustrated in FIG. 6, the catheter 50 may then be removed as indicated by the arrow 72.

One of the many features of the anchor of the instant invention is that it may be moved within or removed from the body lumen in which it is deployed. More specifically, and making reference to FIG. 6, the anchor 34 may be removed by grabbing the support members 42 and pulling the loop 46 over the resilient enlarged portion 48 of the device 30. When the loop 46 is on the proximal side of the enlarged portion 48, further proximal movement of the loop 46 will fully transition the anchor 34 from the second configuration back to the first configuration for removal within the catheter 50.

Alternatively, by virtue of the support members, the anchor 34 may be formed of deformable material such as stainless steel. Using this to advantage, the anchor 34 may be partially collapsed by the catheter 50 to permit the anchor 34 and hence the device 30 to be moved and repositioned in the coronary sinus after which the resilience of the anchor material returns the anchor to its locked and deployed configuration. The anchor may be collapsed by the catheter 50 as illustrated in FIGS. 7 and 8.

Figure 7:
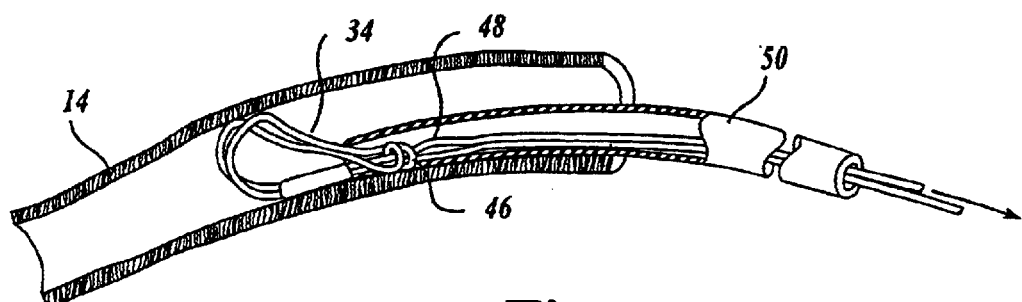
FIG. 7 is a side view similar to FIG. 3 illustrating a first step in the removal of the device anchor.

In FIG. 7, it will be noted that the catheter 50, while the device is held stationary by the tether, is moved distally over the enlarged portion 48 and the loop 46. The anchor 34 is now partially collapsed for movement and repositioning. Once repositioned, the catheter may be withdrawn to redeploy the anchor 34 which returns to its second configuration by virtue of its resiliency and shape memory.

Figure 8:
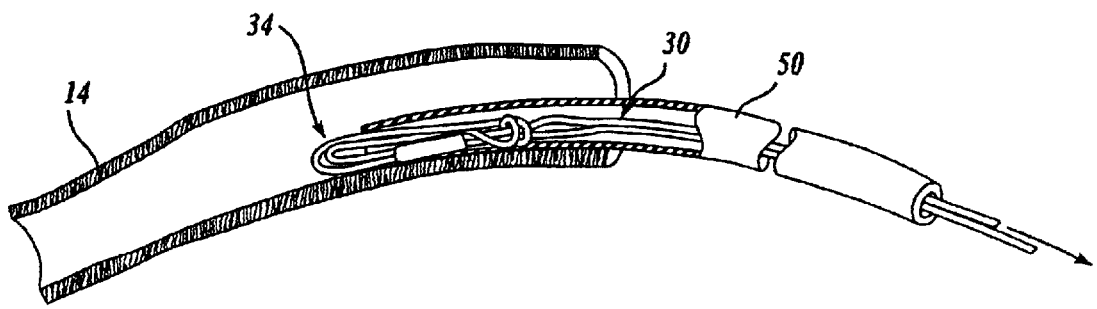
FIG. 8 is a side view similar to FIG. 3 illustrating a final step in the removal of the device anchor.

As seen in FIG. 8, continued distal movement of the catheter 50 causes the anchor 34 to fully collapse. This allows the anchor 34 to be totally drawn into the catheter 50. Once the anchor 34 is collapsed and within the catheter 50, the device 30 may be removed by removing the catheter with the device therein or by pulling the device proximally through the catheter.

FIGS. 9–12 illustrate alternative embodiments of the anchor of the present invention. These embodiments are once again illustrated in connection with the anchoring of a mitral valve annulus therapy device within the coronary sinus of a heart.

Figure 9:
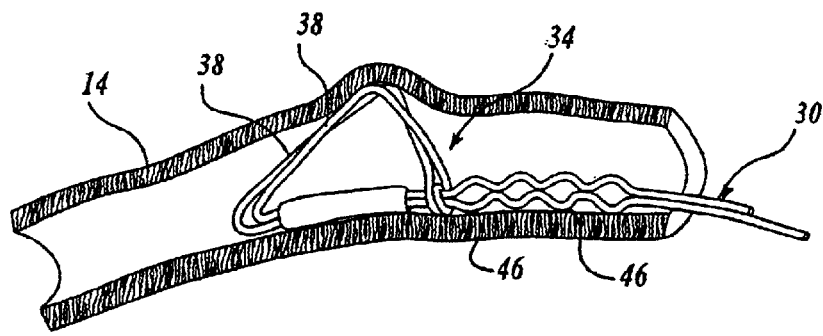
FIG. 9 is a side view similar to FIG. 3 illustrating an alternate embodiment of a deployed device anchor embodying the present invention.

In FIG. 9, the device 30 is shown having a plurality of enlarged portions 46. As a result, a plurality of locks are provided on the device 30 to enable the fixation members to be locked at any one of a plurality of intermediate points between the first configuration and a maximum second configuration illustrated in FIG. 9. This enables the anchor 34 to be sized to a given body lumen.

Figure 10:
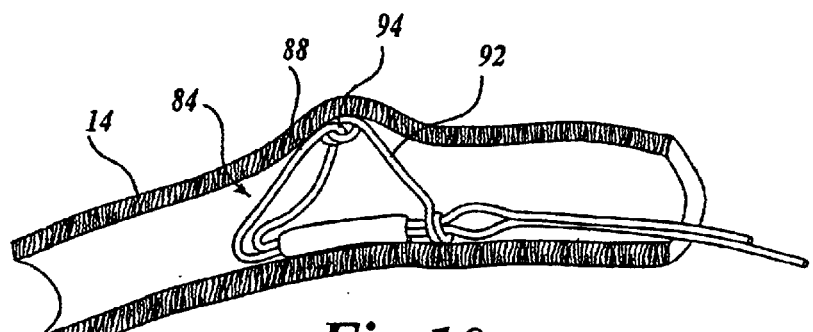
FIG. 10 is a side view similar to FIG. 3 illustrating a further embodiment of a deployed device anchor embodying the present invention.

FIG. 10 shows another anchor 84 embodying the present invention which has a separate fixation member 88 and support member 92. The second or distal end of the fixation member 88 is hingedly coupled to a first or distal end of the support member 92 by a hinged connection 94. The fixation member 88 may have a hoop configuration as the fixation members 38 previously described.

Figure 11:
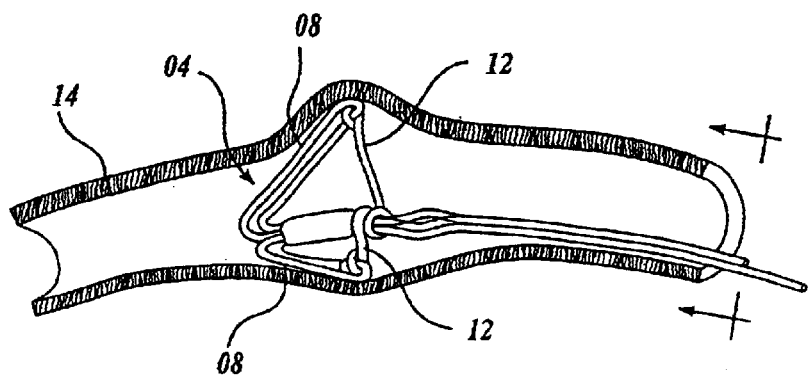
FIG. 11 is a side view similar to FIG. 3 illustrating a still further embodiment of a deployed device anchor embodying the present invention.
Figure 12:
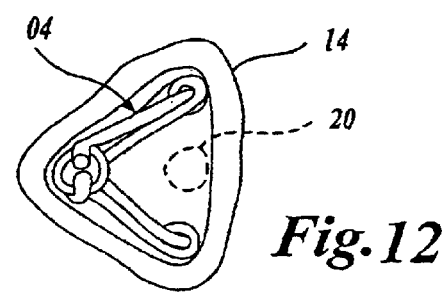
FIG. 12 is an end view of FIG. 11.

FIGS. 11 and 12 illustrated a still further anchor 104 having a pair of fixation members 108 and corresponding separate support members 112. Here, the fixation members 108 are formed by immediately adjacent anchor wires which, as best seen in FIG. 12, are disposed at an angle to permit a cardiac lead, indicated by the dashed circle 120, to pass through the anchor and thus be within the coronary sinus. Hence, a device having an anchor such as anchor 104 is compatible with the provision of a cardiac lead therewith.

As can thus been seen, the present invention provides a new and improved anchor for anchoring a therapeutic device within a body lumen. The anchor of the present invention, by virtue of the lockable support member, creates mechanical advantage to assist deployment of the anchor. This also increases anchor strength. Because the support members may be of hooped or looped configuration, increased contact area between the anchor and the body lumen can be achieved. In addition, the anchor of the present invention allows deactivation and repositioning of the anchor or therapeutic device incorporating the anchor. Still further, because of the locked support structure, the anchor may be formed of smaller diameter wire, tube wall, or other materials which without the locked support provided by the anchor of the present invention would be unsuitable for this application.

While particular embodiments of the present invention have been shown and described, modifications may be made. It is therefore intended in the appended claims to cover all such changes and modifications which fall within the true spirit and scope of the invention.

What is claimed:

1. A device that effects the condition of a mitral valve annulus of a heart comprising:

an elongated body dimensioned to be placed in the coronary sinus of the heart adjacent the mitral valve annulus;

a fixation member carried by the device, the fixation member being adjustable from a first configuration that permits placement of the device in the coronary sinus to a second configuration that anchors the device within the coronary sinus; and a lock that locks the fixation member in the second configuration;

wherein the fixation member is elongated and has a first end hingedly coupled to the device body, wherein the fixation member extends along the device body closely spaced to the device body when in the first configuration and wherein the fixation member is pivoted from the device body when in the second configuration to engage the coronary sinus and anchor the device in the coronary sinus.

2. The device of claim 1 further comprising a support that renders the fixation member substantially rigid when in the second configuration.

3. The device of claim 2 wherein the support is an extension of the fixation member, wherein the fixation member includes a second end opposite the first end and wherein the lock locks the fixation member second end on the device body.

4. The device of claim 3 wherein the fixation member second end is slidable along the device body.

5. The device of claim 3 wherein the device comprises a plurality of the fixation members.

6. An assembly that effects the condition of a mitral valve annulus of a heart, the assembly comprising:

a mitral valve therapy device dimensioned to be placed in the coronary sinus adjacent the mitral valve annulus, the device including an elongated body, a fixation member carried by the device, the fixation member being adjustable from a first configuration that permits placement of the device in the coronary sinus to a second configuration that anchors the device within the coronary sinus, and a lock that locks the fixation member in the second configuration;

a flexible catheter having a lumen that receives the device and being dimensioned to be advanced into the coronary sinus to place the device adjacent the coronary sinus, the catheter transitioning the fixation member from the first configuration to the second configuration; and a tether receivable by the catheter lumen and engagable with the device to pull the device proximally with respect to the catheter;

wherein the fixation member is elongated and has a first end hingedly coupled to the device body, wherein the fixation member extends along the device body when in the first configuration and wherein the fixation member is pivoted from the device body into the second configuration by distal movement of the catheter with respect to the device to engage the coronary sinus and anchor the device in the coronary sinus.

7. The assembly of claim 6 wherein the device further comprises a support that renders the fixation member substantially rigid when in the second configuration.

8. The assembly of claim 7 wherein the support is an extension of the fixation member, wherein the fixation member includes a second end opposite the first end and wherein the lock locks the fixation member second end on the device body when the fixation member second end is in a locked position.

9. The assembly of claim 8 wherein the fixation member second end is slidable along the device body by the catheter into the locked position.

10. The assembly of claim 8 wherein the device comprises a plurality of the fixation members.

11. A device that anchors in a body lumen, the device comprising an anchor and an elongated body dimensioned to be placed in the body lumen, the anchor comprising:

a fixation member, the fixation member being adjustable from a first configuration that permits placement of the device in the body lumen to a second configuration that anchors the device within the body lumen; and a lock that locks the fixation member in the second configuration, wherein the fixation member is elongated and has a first end hingedly coupled to the device body, wherein the fixation member extends along the device body closely spaced to the device body when in the first configuration and wherein the fixation member is pivoted from the device body when in the second configuration to engage the body lumen and anchor the device in the body lumen, the anchor further comprising a support that renders the fixation member substantially rigid when in the second configuration.

12. The device of claim 11 wherein the support is an extension of the fixation member, wherein the fixation member includes a second end opposite the first end and wherein the lock locks the fixation member second end on the device body.

13. The device of claim 12 wherein the fixation member second end is slidable along the device body.

14. The device of claim 12 comprising a plurality of the fixation members.

* * * * *